United States Patent
Weber et al.

(10) Patent No.: US 11,185,827 B2
(45) Date of Patent: Nov. 30, 2021

(54) MODIFIED FILTER MEMBRANE AND THE USE THEREOF

(71) Applicant: Boehringer Ingelheim Vetmedica GmbH, Ingelheim am Rhein (DE)

(72) Inventors: Christoph Weber, Hannover (DE); Heinz Schoeder, Isernhagen (DE); Jens Altrichter, Kavelstorf (DE); Roland Kirchner, Edling (DE); Stefan Margraf, Frankfurt am Main (DE); Michael Scholl, Oberhaching (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 65 days.

(21) Appl. No.: 16/036,029

(22) Filed: Jul. 16, 2018

(65) Prior Publication Data
US 2019/0015790 A1 Jan. 17, 2019

(30) Foreign Application Priority Data
Jul. 17, 2017 (EP) .................................. 17181670

(51) Int. Cl.
*B01D 67/00* (2006.01)
*A61M 1/34* (2006.01)
(Continued)

(52) U.S. Cl.
CPC .......... *B01D 67/0093* (2013.01); *A61M 1/34* (2013.01); *B01D 61/40* (2013.01); *B01D 67/0088* (2013.01); *B01D 69/02* (2013.01); *B01D 71/40* (2013.01); *B01D 71/68* (2013.01); *G01N 33/491* (2013.01); *B01D 2221/10* (2013.01); *B01D 2323/02* (2013.01); *B01D 2325/022* (2013.01); *B01D 2325/36* (2013.01)

(58) Field of Classification Search
CPC ............ B01D 67/0093; B01D 67/0088; B01D 2323/02; B01D 69/02; B01D 61/40; B01D 71/40; B01D 71/68; B01D 2325/36; B01D 2325/022; B01D 2221/10; A61M 1/34; G01N 33/491
See application file for complete search history.

(56) References Cited

U.S. PATENT DOCUMENTS 7,316,919 B2 * 1/2008 Childs ................ B01D 67/0006
435/177
2007/0264629 A1 * 11/2007 Holmes ................ B01L 3/5027
435/5
(Continued)

FOREIGN PATENT DOCUMENTS

EP 2 264 453 A1 12/2010

OTHER PUBLICATIONS

Arman Nabatiyan, Zaheer A. Parpia, Robert Elghanian, David M. Kelso, Membrane-Based Plasma Collection Device for Point-of-Care Diagnosis of HIV, Journal of Virological Methods, vol. 173, No. 1, Jan. 4, 2011, pp. 37-42.

*Primary Examiner* — Krishnan S Menon
(74) *Attorney, Agent, or Firm* — David S. Safran; Roberts Calderon Safran & Cole, P.C.

(57) ABSTRACT

A surface-modified filter membrane for filtering blood, in particular for separating blood plasma and blood serum, and a method for the production thereof, a filter provided therewith and the use thereof.

2 Claims, 4 Drawing Sheets

(51) Int. Cl.
*G01N 33/49* (2006.01)
*B01D 69/02* (2006.01)
*B01D 61/40* (2006.01)
*B01D 71/40* (2006.01)
*B01D 71/68* (2006.01)

(56) References Cited

U.S. PATENT DOCUMENTS

| | | |
|---|---|---|
| 2012/0024788 A1 | 2/2012 | Kelso et al. |
| 2012/0118825 A1* | 5/2012 | Margraf ............... B01D 63/087 210/645 |
| 2014/0178992 A1* | 6/2014 | Nakashima .......... C12N 5/0663 435/375 |
| 2016/0310904 A1 | 10/2016 | Liu et al. |
| 2017/0266626 A1 | 9/2017 | Kayama et al. |
| 2017/0343533 A1 | 11/2017 | Liu et al. |

* cited by examiner

MODIFIED FILTER MEMBRANE AND THE USE THEREOF

BACKGROUND OF THE INVENTION

Field of the Invention

The present invention relates to the technical field of filtration methods, in particular the filtering of blood.

The present invention relates in particular to a surface-modified filter membrane for filtering blood, in particular for separating blood plasma and blood serum.

Furthermore, the present invention relates to a method for surface-modifying a filter membrane and to a filter which contains a surface-modified filter membrane, and to the use of said filter.

The present invention also relates to a kit which contains a filter having a surface-modified filter membrane, and to the use of said filter.

Description of Related Art

For example, European Patent Application EP 2 264 453 A1 describes a blood filter and a filtration method which is principally suited for obtaining blood plasma by filtration from blood.

However, it has been demonstrated that blood plasma obtained by filtration, in comparison with centrifuged blood plasma, exhibits a different distribution of metabolic products, in particular proteins. In particular, a significant depletion, i.e. reduction, in peptide content is found in blood plasma obtained by filtration in comparison with blood plasma obtained from centrifugation. A reduction in peptide content of up to 20% of the values from the centrifuged plasma is usually observed. However, this makes it impossible to quantitatively determine the individual metabolic products in order to determine metabolic changes and metabolic disorders, or it distorts the results. This applies in particular because the various components of the blood plasma obtained by filtration are depleted to different degrees in comparison with the centrifuged blood plasma, which is why the normal or pathological values for the individual blood plasma components cannot simply be scaled with respect to the filtered blood plasma.

Furthermore, in a plurality of samples haemolysis occurs during filtration, i.e. the red blood cells are destroyed during filtration. This is in particular facilitated in that, in the filtration method described in European Patent Application EP 2 264 453 A1 and corresponding U.S. Patent Application Publication US 2012/118825 (A1), the blood is pressed through a filter membrane by applying pressure. However, in this case, haemolysis occurs frequently, particularly when blood samples are not ideal, as a result of which the plasma obtained cannot be used. In the existing filter system it is also impossible, or it is very difficult, to obtain a sufficiently high quantity of blood plasma in a short time.

Blood tests play a decisive role in the diagnosis of diseases and metabolic changes.

While it is possible to use untreated blood samples for a variety of tests, blood plasma tests are necessary in order to diagnose a range of metabolic changes or metabolic disorders.

Blood plasma is the liquid portion of the blood which is obtained by centrifuging blood samples that have been made incoagulable. Blood plasma is usually yellowish clear and no longer has blood cells such as erythrocytes, thrombocytes and leucocytes. However, metabolic products such as glucose, lipids and proteins, in particular hormones, can be detected or identified in blood plasma. The presence of diseases or metabolic changes can be deduced from the presence of certain metabolic products in the blood plasma or from the particular concentrations of said products.

In comparison with other blood tests, blood plasma tests are very complex and are therefore carried out almost exclusively in special laboratories. This is complicated by the fact that blood plasma is typically obtained by centrifuging blood samples that have been made incoagulable. However, this means that already the blood plasma can usually only be obtained and subsequently analyzed in laboratories, even if the actual test does not have to be carried out in a laboratory. Hence, the entire diagnostic process is typically bound to a laboratory and/or can only be carried out in a stationary manner on account of the procedure for obtaining blood plasma.

For a variety of applications, however, in particular also for rapid tests, the detour via a laboratory is complex, costly, time-intensive and often unacceptable or not reasonable.

This is particularly the case for what are known as point-of-care systems which are mobile, autonomous systems for treating samples at the sample collection site, in particular for determining diseases or pathogens. Point-of-care systems are currently being developed, specifically for the veterinary field, which make it possible, on the basis of microfluidic systems, to simultaneously determine a wide range of diseases or metabolic changes by means of tests on bodily fluids of animals. While it is possible to effectively obtain data on pathogens on the basis of saliva or blood samples by means of point-of-care systems using PCR techniques, it is however still problematic to qualitatively and quantitatively detect or identify certain metabolic products, in particular peptides, which detection processes are typically carried out on blood plasma, since obtaining blood plasma is coupled to the centrifugation. Although in principle it is also possible to design centrifuges to be mobile and to install said centrifuges in special veterinary vehicles or mobile laboratories, for example, this contradicts the principle of point-of-care systems which ought to make it possible to actually carry the entire measuring and evaluation equipment in a mobile manner. In order to really be mobile, the procedure for obtaining blood plasma has to therefore be decoupled from the centrifugation as far as possible. Besides centrifugation, in particular also the filtration of blood comes into consideration for obtaining blood plasma.

SUMMARY OF THE INVENTION

It is therefore an object of the present invention to avoid the previously described disadvantages associated with the prior art, or at least to mitigate said disadvantages.

It is furthermore an object of the present invention to provide a filter membrane and a filter which prevents a depletion, i.e., a reduction, in the content of metabolic products, in particular peptides, in the blood plasma in comparison with the blood plasma obtained by centrifugation, or which makes the depletion uniform for the different peptides and not pronounced.

It is furthermore another object of the present invention to provide a filter membrane and a filter which make it possible to quickly obtain sufficiently large blood plasma samples for analysis purposes.

It is furthermore another object of the present invention to provide a filter membrane and a filter which make it possible to obtain blood plasma at significantly lower rates of hemolysis.

Another object addressed by the present invention is to provide a kit for a point-of-care system, which kit makes it possible to obtain and analyze blood plasma samples in a mobile manner, in particular at the sample collection site.

According to a first aspect of the present invention, a subject of the present invention is therefore a filter membrane as described herein.

According to a second aspect of the present invention, a further subject of the present invention is a method for producing a surface-modified filter membrane as described herein.

According to a third aspect of the present invention, yet a further subject of the present invention is a filter as described herein.

According to a fourth aspect of the present invention, a further subject of the present invention is the use of a filter for filtering blood as described herein.

Finally, according to a fifth aspect of the present invention, a further subject of the present invention is a kit, comprising a filter and a cartridge, for testing blood plasma as described herein.

It goes without saying that particular embodiments or the like referred to in the following, which are described only in connection with one aspect of the invention, also apply correspondingly in relation to the other aspects of the invention, without the need for this to be expressly mentioned.

It should further be noted that all relative stated quantities or percentages referred to hereinafter, in particular quantities stated in terms of weight, are intended to be selected by a person skilled in the art in the context of the present invention such that the sum of the ingredients, additives and/or auxiliaries or the like is always 100% or 100 wt. %. However, this is apparent to a person skilled in the art.

Moreover, a person skilled in the art can deviate from the numbers, ranges or quantities stated hereinafter on a case-by-case basis, and depending on application, without departing from the scope of the present invention.

Furthermore, all of the stated parameters, or the like, referred to in the following can be determined or established in principle by standardized or explicitly indicated determination methods, or determination methods familiar to a person skilled in the art per se.

That being said, the subject matter of the present invention is explained in more detail below.

According to a first aspect of the present invention, a subject of the present invention is a filter membrane for filtering blood, in particular for separating blood plasma and blood serum, wherein the filter membrane is surface-modified, in particular coated.

This is because, as the applicant has surprisingly found out, by surface-modifying, in particular coating, filter membranes it is possible to substantially avoid the depletion of substances, in particular metabolic products, such as peptides and in particular hormones, in filtered blood plasma in comparison with centrifuged blood plasma. At the very least, however, it is made possible to mitigate the depletion of the substances, i.e. the reduction in the content thereof, in the blood plasma, and to unitise the depletion of all the components of the blood plasma, in such a way that both qualitative and quantitative detection processes can be carried out on the filtered blood plasma, and specifically without normal or pathological values for each substance, i.e., for each metabolic product of the plasma, having to be determined in complex clinical trials.

The filter membrane which, according to the invention, is surface-modified, in particular coated, thus makes it possible to analyze blood plasma by means of what are known as point-of-care systems, i.e., mobile and preferably autonomous measuring and evaluation systems which are preferably compact enough to be transported by a single person without any further assistant or auxiliary means.

The present invention therefore makes it possible to broaden the range of point-of-care systems to also include testing blood plasma; this is a notable improvement in particular for the veterinary field since it makes it possible henceforth to carry out blood plasma tests at the sample collection site, i.e. directly in the stable or in the field.

It is furthermore possible by means of the filter membrane according to the invention to almost completely suppress hemolysis during blood filtration, such that blood plasma can actually be obtained for subsequent testing from almost all filtered samples.

Furthermore, the system according to the invention makes it possible to obtain sufficiently large quantities of blood plasma, in particular animal blood plasma, in a short amount of time, in order to subsequently carry out tests by means of microfluidic systems.

In the context of the present invention, blood plasma is understood to mean the liquid portion of human or animal blood which is obtained by centrifugation or filtration of blood samples that have been made incoagulable.

In the context of the present invention, a surface modification is understood to mean in particular a change in the physical and/or chemical properties, such as hydrophilicity, of a boundary face. Surface modifications can be carried out for example by means of addition or binding of chemical substances.

As explained previously, in the context of the present invention, the filter membrane is surface-modified, in particular coated. In this connection it is typically provided for the filter membrane to be surface-modified by a modifying reagent.

In particular, in this connection, the modifying reagent can be deposited on or added to the filter membrane, or chemically or physically bonded thereto. However, it is likewise possible for the modifying reagent to be formed directly on the filter membrane, for example by polymerizing monomers. However, it is typically provided for the surface modification to be performed by an already pre-produced modifying reagent.

In the context of the present invention, particularly good results are achieved if the modifying reagent is selected from the group consisting of polyacrylic acids, polymethacrylic acids, acrylates, methacrylates, in particular polyhydroxymethacrylates, acrylamides, polyvinyl alcohols, polyvinylpyrrolidone, polyvinyllactate, polyethylene glycols, polysorbates, and mixtures thereof.

In this connection, it is preferable for the modifying reagent to have hydroxy functions, amine functions and/or thiol functions, in particular hydroxy functions. In the context of the present invention, it is preferable to use a modifying reagent that has polar functional groups. In this way, the filter membrane can be blocked effectively for adsorption of the metabolic products which are present in the blood plasma. Furthermore, haemolysis during filtration by applying pressure is also significantly reduced.

According to a preferred embodiment of the present invention, the modifying reagent is selected from polyacrylic acids, polymethacrylic acids, poly(2-hydroxyethyl)

methacrylate, poly(2-hydroxyethyl) acrylate, poly(2-hydroxypropyl) methacrylate, poly(2-hydroxypropyl) acrylate, poly(4-hydroxybutyl) methacrylate, poly(4-hydroxybutyl) acrylate, polyvinyl alcohol, hydroxy-terminated polyethylene glycols, polysorbate 20, polysorbate 80 and copolymers or mixtures thereof.

In this connection, polysorbate 20 is polyoxyethylene (20) sorbitan monooleate and polysorbate 80 is polyoxyethylene (80) sorbitan monolaurate.

Preferably, the modifying reagent is a hydrogel former. By using a hydrogel former, the layer formed by surface modification swells on the filter membrane when contact is made with the water in the blood and therefore protects the red blood cells against mechanical destruction at the filter membrane, in particular during filtration under pressure, such that haemolysis can be avoided. In this connection, the hydrogel formers can be selected in particular from the group of polymethacrylates, in particular polyhydroxymethacrylates, polymethacrylic acid, polyvinylpyrrolidone, polyvinyl alcohol, polyethylene glycol and mixtures thereof.

In the context of the present invention, particularly good results are achieved if the modifying reagent is selected from poly(2-hydroxyethyl) methacrylate, hydroxy-terminated polyethylene glycols, polysorbate 20, polysorbate 80 and copolymers and mixtures thereof. Particularly suitable copolymers are for example copolymers from 2-hydroxyethylmethacrylate together with methyl methacrylate or ethylene glycol dimethacrylate. Furthermore, copolymers from acrylic acids and acrylates, in particular methacrylate, are likewise suitable.

In the context of the present invention it is very particularly preferable for the modifying reagent to be a poly(hydroxyethyl) methacrylate or a copolymer of 2-hydroxyethyl methacrylate. The modifying reagent is in particular poly(hydroxyethyl) methacrylate.

In regard to the filter membrane used and surface-modified in the context of the present invention, the membrane is preferably an asymmetrical membrane, in particular a porous asymmetrical membrane. In the context of the present invention, an asymmetrical membrane is understood to mean a membrane of which the pore size changes inside the membrane, in particular in a direction perpendicular to the membrane surface. The size of the pores inside the membrane, in particular the filter membrane, preferably changes continuously and not abruptly.

Preferably, in the context of the present invention, the filter membrane usually consists of a synthetic polymer material, in particular of a hydrophilic, synthetic polymer material.

In the context of the present invention, particularly good results are achieved if the material of the filter membrane comprises a polymer from the group of polyamide, polyethylene terephthalate, polysulfone, polyether sulfone, polyvinyl pyrrolidone, polyurethane, polyacrylonitrile, poly(vinylidene fluoride), polytetrafluoroethylene, polyacrylonitrile-methacrylate copolymer, cellulose, modified cellulose, cellulose ether and mixtures and copolymers thereof.

In the context of the present invention, it is particularly preferable for the filter membrane to comprise at least one hydrophilic polymer. In the context of the present invention, a hydrophilic polymer is understood to mean a polymer that has polar functionalities, such as hydroxy functions, amine functions, ketones or thiols. Due to the polar chemical functions, the polymer can interact with other polar substances, in particular water or polar solvents such as ethanol, and can be dissolved or dispersed in polar solvents. If, in the context of the present invention, mixtures or copolymers of the above-mentioned polymers are used, it has thus proven itself if at least one of the polymers is a hydrophilic polymer.

Particularly well-suited filter membranes comprise for example polysulfone in combination with at least one hydrophilic polymer. In this connection, it is particularly preferable for the material of the filter membrane to be a mixture of polysulfone and polyvinyl pyrrolidone.

A filter membrane that is particularly suitable in the context of the present invention is described, for example, in International Patent Application Publication WO 98/25758 A1 and corresponding U.S. Pat. No. 6,045,899. Particularly suitable polysulfone-based filter membranes that exhibit no surface modification can furthermore be obtained from Pall Corporation, Washington, New York, USA or Pall GmbH, Dreieich, Germany.

According to a second aspect of the present invention, a further subject of the present invention is a method for producing a surface-modified, in particular coated, filter membrane, as described previously, wherein
  i. in a first method step, a filter membrane is provided and treated by means of a modifying reagent,
  ii. in a second method step, which follows the first method step (a), excess modifying reagent is removed, and
  iii. optionally or if necessary, in a third method step, which follows the second method step (b), the filter membrane is dried.

In the context of the present invention, in the first method step (i), the modifying reagent is preferably present in a solution or a dispersion. If in method step (i) the modifying reagent is in the form of a solution or a dispersion, drying the surface-modified membrane after removing the excess modifying reagent is advantageous and usually also necessary in order to remove the residue from the solvent or dispersant.

According to one particular embodiment of the present invention, the modifying reagent is formed in the presence of the filter membrane, preferably on the filter membrane, in particular by a polymerization reaction in the presence of the filter membrane. According to said embodiment of the present invention, monomers of the above-mentioned modifying reagents are provided in a solution or dispersion or as pure substances and are polymerized in the presence of the filter membrane, whereby a surface modification, in particular a coating, is established or built directly on the filter membrane.

If the modifying reagent in method step (i) is in the form of a solution or dispersion, the solution or dispersion preferably contains a solvent or dispersant selected from the group of water, alcohols, in particular $C_1$ to $C_{10}$ alcohols, preferably methanol, ethanol and/or 2-propanol, acetone, ethyl acetate, N,N-dimethylformamide and mixtures thereof. In the context of the present invention, particularly good results are achieved if the solvent or dispersant is selected from the group of water and alcohols and mixtures thereof, preferably mixtures thereof.

In this connection, in particular, particularly good results are achieved if the solvent or dispersant is selected from water and alcohols of the group of methanol, ethanol and/or 2-propanol. The solvent or dispersant is preferably a mixture of ethanol and water.

If the solvent or dispersant is a mixture of alcohol and water, in particular ethanol and water, it is preferable for the solvent or dispersant to have an alcohol to water weight ratio in the range of 99.5:0.5 to 80:20, in particular 99:1 to 85:15, preferably 98:2 to 90:10, particularly preferably 97:3 to 94:6.

In the context of the present invention, a solution is understood to mean a one-phase system in which a dissolved substance is homogeneously distributed in a solvent and usually scattered on a molecular level or in the form of ions. In the context of the present invention, a dispersion is understood to mean a two-phase system in which a first phase, namely the dispersed phase, is finely distributed in a second phase, namely the continuous phase, also referred to as the dispersant. It is often very difficult to distinguish between solution and dispersion, in particular when using polymers as the dissolved or dispersed substance, i.e. the dispersed phase, since the transition from solution to dispersion is continuous.

If, in method step (i), the modifying reagent is present in a solution or dispersion, the solution or dispersion usually contains the modifying reagent in quantities of 0.01 to 10 wt. %, in particular 0.1 wt. % to 5 wt. %, preferably 0.1 to 4 wt. %, more preferably 0.2 to 3 wt. %, particularly preferably 1 to 3 wt. %, based on the solution or dispersion.

In regard to the duration for which the filter membrane is treated in method step (i), said duration by its nature can vary within wide ranges. However, it has proven itself if, in method step (i), the filter membrane is treated with the modifying reagent for a period of 1 minute to 20 hours, in particular 5 minutes to 15 hours, preferably 10 minutes to 10 hours, more preferably 30 minutes to 5 hours, particularly preferably 45 minutes to 2 hours, most particularly preferably 1 hour. In the above-mentioned treatment durations, in particular sufficiently strong surface modifications, in particular sufficiently thick coatings, which however do not clog or block up the pores in the filter membrane, can be produced on the filter membrane.

Method step (i) is preferably carried out at temperatures in the range of 10° C. to 40° C., in particular 15° C. to 30° C., preferably 20° C. to 25° C.

According to one preferred embodiment of the present invention, in method step (b), excess modifying reagent is removed from the filter membrane by rinsing with the solvent or dispersant. In this connection, particularly good results are achieved if the solvent or dispersant in method step (ii) is the same solvent or dispersant that was already used in method step (i). According to a particularly preferred embodiment of the present invention, an alcohol is used to remove the excess modifying reagent. In this connection, it is preferable for the alcohol to be selected from $C_1$ to $C_{10}$ alcohols, in particular methanol, ethanol, 2-propanol and mixtures thereof. Ethanol is preferably used to remove excess modifying reagent.

In this connection, the filter membrane can be rinsed with the solvent or dispersant once or a plurality of times, in particular two to three times. In the context of the present invention, however, it is particularly preferable for the filter membrane to be rinsed with the solvent or dispersant once during method step (ii). When rinsed once with the solvent or dispersant, excess modifying reagent that is not added or bonded to the membrane is reliably removed from the membrane surface, without modifying reagent that is already added or bonded to the membrane being removed again from the membrane.

If, in the context of the present invention, the filter membrane is freed from excess modifying reagent by means of a plurality of rinses with the solvent or dispersant, it has proven itself if small quantities of the modifying reagent are added to the solvent or dispersant.

In regard to the time period over which the filter membrane is rinsed, it has proven itself if the filter membrane is rinsed with the solvent or dispersant during method step (ii) for a period of 5 seconds to 1 hour, in particular 5 seconds to 1 minute, preferably 10 to 20 seconds.

Method step (b) is preferably carried out at temperatures in the range of 10° C. to 40° C., in particular 15° C. to 30° C., preferably 20° C. to 25° C.

Furthermore, in the context of the present invention, method steps (i) and (ii) can be carried out alternately multiple times, in particular two to five times, preferably two to three times. Multiple surface modification or multiple coating can therefore take place if necessary. However, for reasons of cost and time efficiency, it is preferable for only one surface modification step to be carried out. If suitable modifying reagents are selected, and/or suitable concentrations of modifying reagents are selected, a sufficiently good surface modification, in particular coating, can be achieved by means of a single treatment step, i.e. carrying out method step (i) once.

In regard to drying in method step (iii), in particular the removal of solvents or dispersants, this can be carried out in a broad temperature range. It has proven itself, however, if the filter membrane is dried in method step (c) at temperatures in the range of 1° C. to 95° C., in particular 10° C. to 60° C., preferably 15° C. to 50° C., more preferably 20° C. to 30° C.

Furthermore, the filter membrane can also be dried under reduced pressure. If in method step (iii) the filter membrane is dried under reduced pressure, it has proven itself if the filter membrane is dried at a pressure in the range of 10 to 900 mbar, in particular 20 to 500 mbar, preferably 50 to 400 mbar, more preferably 100 to 300 mbar.

By drying the filter membrane in the above-mentioned temperature ranges and optionally at the above-mentioned pressures, very quick and gentle drying of the filter membrane can be achieved.

Furthermore, the filter membrane can be cut to size in an optional fourth method step (iv), which follows the third method step (iii). In particular, the filter membrane can be cut to size in method step (iv) so as to be ready for installation in filters or filter systems. In this connection, the filter membrane can be cut to size for example by means of laser cutting or punching.

Advantageously, the surface modification, in particular coating, of the filter membrane is preferably performed on a filter membrane sheet, from which, during method step (iv), 40 to 400, in particular 50 to 350, preferably 60 to 300, filter membranes for filter purposes, in particular for installation in filter systems, are then obtained.

For more extensive details regarding the method according to the invention, reference can be made to the explanations above with respect to the filter membrane according to the invention, which apply correspondingly in relation to the method according to the invention.

According to a third aspect of the present invention, yet a further subject of the present invention is a filter for filtering blood, in particular for separating blood plasma and blood serum, comprising a previously described filter membrane.

Preferably or advantageously, the filter membrane of the filter has a surface area of 8 to 30 $cm^2$, in particular 10 to 25 $cm^2$, preferably 10 to 20 $cm^2$, more preferably 12 to 18 $cm^2$.

In particular, by means of the filter membrane in the above-mentioned dimensions, it is possible, with moderate application of pressure, to quickly obtain 300 μl to 500 μl of blood plasma from 2 to 4 ml of blood. The above-mentioned quantity of blood plasma is usually required in order to analyze the blood plasma by means of microfluidic systems.

Furthermore, in the context of the invention, the filter can be in particular at least substantially disc-shaped. The disc-shaped construction, preferably comprising openings having adapters on the upper and lower face, i.e., the flattened faces of the disc, makes it possible to quickly filter over a large filter membrane surface area, such that the filtration takes place gently overall and hemolysis is avoided, even under application of pressure. Furthermore, the disc-shaped construction of the filter, in particular of the filter housing, makes it possible to filter effectively at low filter volumes.

In particular, in the context of the present invention, the filter has a volume of 800 to 3000 µl, in particular 1000 to 2000 µl, preferably 1200 to 1500 µl.

Advantageously, the filter, in particular the filter housing, preferably comprises a filter upper part and a filter lower part, the filter lower part in particular having a curvature, in particular a convex curvature. By the curvature of the filter lower part the pressure during filtration is slightly reduced, such that hemolysis is largely avoided.

In the context of the present invention, particularly good results are achieved if the radius of curvature of the filter lower part is 80 to 200 mm, in particular 100 to 180 mm, preferably 110 to 150 mm, more preferably 115 to 130 mm.

The radius of curvature of the filter lower part is preferably ⅝ to ⅞, in particular ⅚, of the internal volume of the filter.

For more extensive explanations regarding the filter according to the invention, reference can be made to the explanations above with respect to the remaining aspects of the invention, which explanations apply correspondingly in relation to the filter according to the invention.

According to a fourth aspect of the present invention, a further subject of the present invention is the use of a previously described filter for filtering blood, in particular for separating blood plasma and blood serum.

According to a preferred embodiment of the present invention, the previously described filter is used in veterinary applications, in particular for testing animal blood.

In particular, the previously described filter can be used for filtering animal blood, in particular for separating blood plasma and blood serum in animal blood. Animal blood is preferably blood from pigs, cattle, horses, dogs, cats or poultry. If blood from poultry is used, it is preferable to use blood from chickens, turkeys, geese or ducks.

For more extensive details regarding this aspect of the invention, reference can be made to the explanations above with respect to the remaining aspects of the invention, which explanations apply correspondingly in relation to the use according to the invention.

Finally, according to a fifth aspect of the present invention, a further subject of the present invention is a kit, containing a previously described filter and a cartridge, in particular a cartridge for testing bodily fluid.

In the context of the present invention, the cartridge preferably comprises a main body having a plurality of channels and cavities, wherein the cartridge comprises a cover for the channels and cavities.

According to a preferred embodiment of the present invention, the kit also contains a container, in particular a syringe, for collecting blood and/or for transferring the blood sample into the filter.

According to a preferred embodiment of the present invention, the kit according to the invention is used in veterinary applications, in particular for testing animal blood.

In the context of the present invention, the kit according to the invention can be used to obtain blood plasma from animal blood and to subsequently test the blood plasma.

If the kit according to the invention is used to obtain and test animal blood plasma, the animal blood is usually selected from the blood of pigs, cattle, horses, dogs, cats or poultry. In this connection, it is preferable for the blood of poultry to be selected from the blood of chickens, turkeys, geese or ducks.

For further details regarding this aspect of the invention, reference can be made to the explanations above with respect to the remaining aspects of the invention, which explanations apply correspondingly in relation to the kit according to the invention.

The subject matter of the present invention is explained in a non-limiting, exemplary manner in the following with reference to a preferred embodiment, in which:

DETAILED DESCRIPTION OF THE INVENTION

Figure 1:
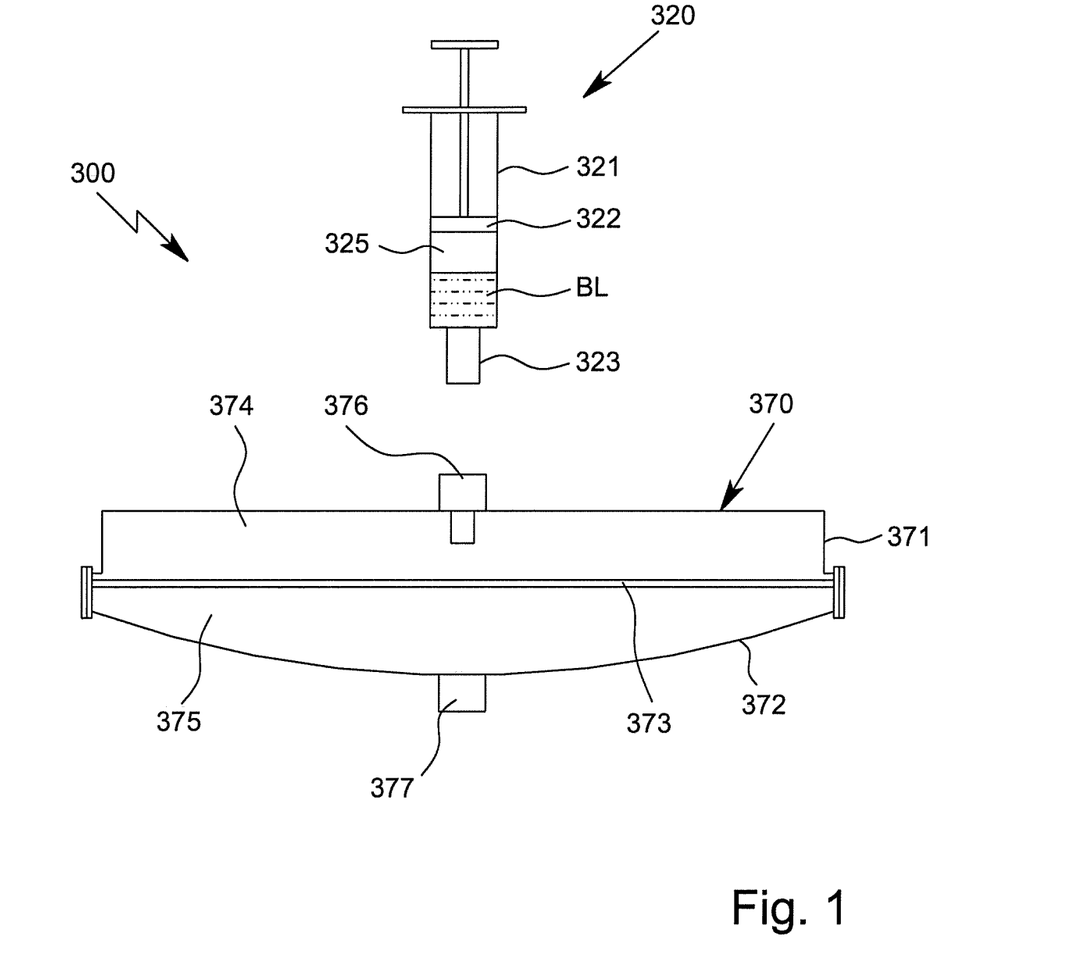
FIG. 1 is a schematic sectional view of a filter according to the invention and a transfer instrument.

FIG. 1 schematically shows a filter 370 according to the invention. The filter 370 preferably has a filter housing, in particular comprising a filter upper part 371 and a filter lower part 372.

The filter 370 comprises a filter membrane 373 which extends in particular perpendicularly with respect to a filtering direction of the medium to be filtered, in particular of blood BL.

In producing the filter 370, the filter membrane 373 is preferably adhesively secured into the filter lower part 372, the adhesion preferably taking place or being flush with the filter lower part 372, and the filter lower part 372 subsequently being heat sealed to the filter upper part 371.

The filter upper part 371 and the filter lower part 372 preferably consist of thermoplastic materials, in particular of the same thermoplastic material.

The filter membrane 373 generally has a diameter of 30 to 60 mm, in particular 35 to 55 mm, preferably 40 to 50 mm, more preferably 45 to 50 mm.

The filter membrane 373 is preferably surface-modified by treatment with a dispersion of 2 wt. % poly(2-hydroxyethyl) methacrylate, based on the total weight of the dispersion, in ethanol.

Filter chambers 374 and 375 are formed by the filter housing above the filter membrane 373 as well as below the filter membrane 373, which chambers are used to receive and dispense liquids, in particular blood BL or blood plasma, as a sample P to be tested.

Figure 2:
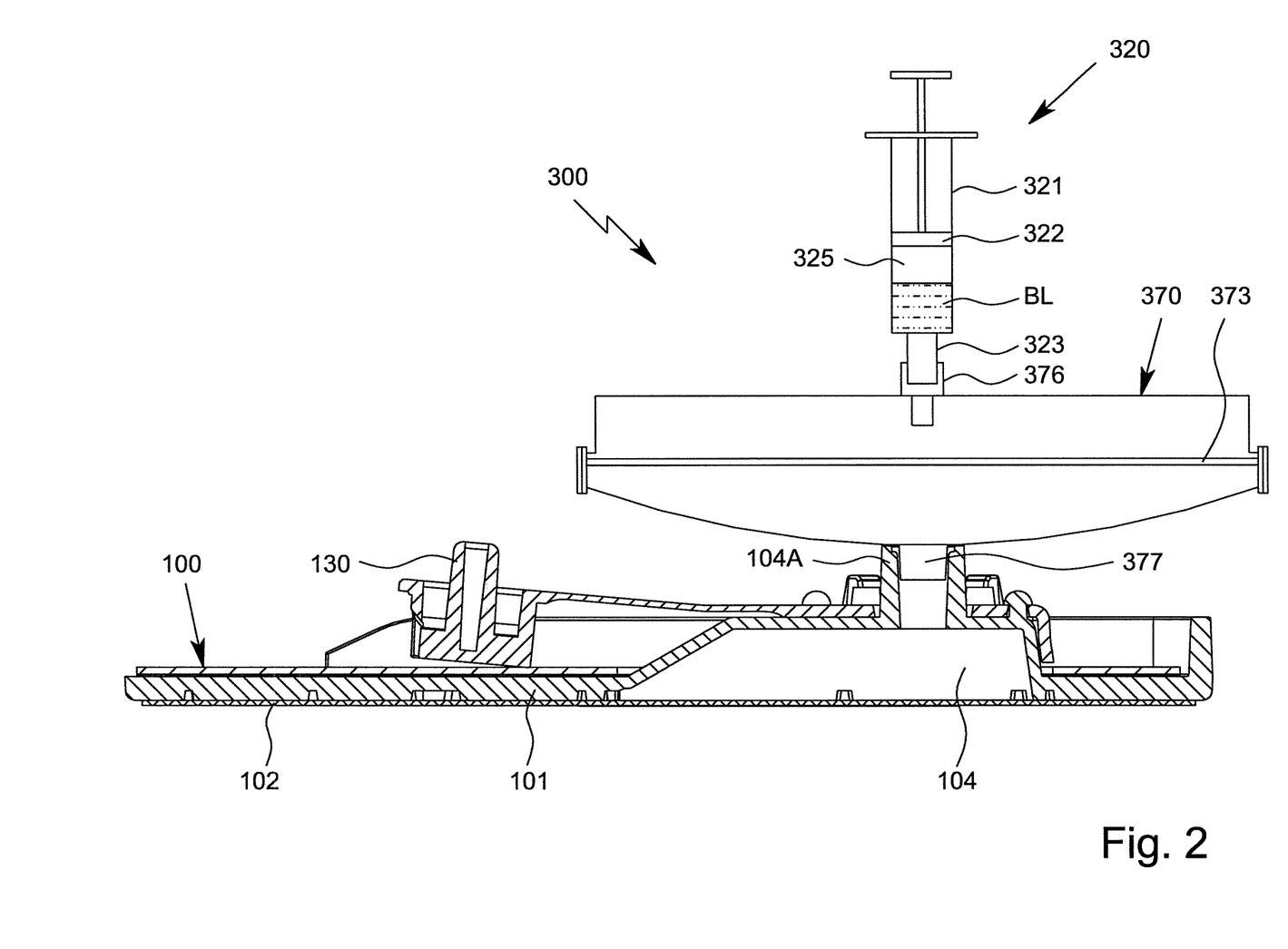
FIG. 2 is a schematic view of the components of a kit according to the invention, comprising a cartridge having a filter connected thereto and a transfer instrument shown in an in use condition.

The filter 370 preferably comprises on the upper face thereof an opening or inlet 376, in particular a blood inlet opening, for receiving the medium or blood BL to be filtered and, on the lower face thereof, preferably comprises an outlet 377, in particular a plasma outlet opening, for dispensing the filtrate or blood plasma as the sample P (not shown in FIGS. 1 and 2).

The inlet 376 is preferably associated with the filter chamber 374 which receives the medium or blood BL to be filtered. The outlet 377 is preferably connected to the filter chamber 375 which is downstream of the filter membrane 373.

The medium or blood BL to be filtered is preferably fed or conducted by means of a transfer instrument 320, which is likewise schematically shown in FIG. 1 and can be designed for example as a container, syringe or the like.

The transfer instrument 320 is designed to receive or provide a sample, or medium or blood BL to be filtered, and comprises in particular a housing 321. Furthermore, the transfer instrument 320 preferably comprises a means, such as a piston 322, in particular for ejecting and/or for regulating the pressure and the volume provided for the sample. The transfer instrument 320 further comprises a connection 323 for receiving and/or dispensing the medium or sample to be filtered. The connection 323 is preferably designed in such a way that it can be fluidically connected to the inlet 376 of the filter 370.

According to a preferred embodiment of the present invention, the filter 370 according to the invention is put together or prepackaged with a cartridge 100 (see FIG. 2) and/or with the transfer instrument 320, in the form of a kit 300, and is offered or available in a ready-to-use state.

By means of the filter 370 and/or the kit 300, blood plasma samples can be analyzed directly from freshly obtained blood samples BL which have optionally been made incoagulable by an addition of e.g. sodium citrate.

In order to obtain blood plasma as a sample P, which is to be tested preferably in the cartridge 100, by means of the filter 370 according to the invention, a blood sample BL, in particular having a volume of 1 to 5 ml of blood, preferably 1.5 to 4 ml, more preferably 2 to 3 ml of blood, particularly preferably 2 ml of blood, which has been made incoagulable, e.g., by adding sodium citrate, is preferably provided to the filter 370 by means of the transfer instrument 320 or in another manner.

In particular, the blood BL can be received in the housing 321 of the transfer instrument 320 by actuating, in particular pulling, the means or piston 322. By further actuating the means or piston 322 and thereby creating a partial vacuum, the volume available in the housing 321 is increased such that a gas space 325 is formed. The gas space 325 is preferably filled with air.

The volume of the gas space 325 is approx. two to three times, in particular 2.5 times, the volume of the blood sample BL. The gas, in particular the air, in the gas space 325 is used to generate pressure during the filtering process, the pressure in the filter 370 and at the filter membrane 373 only increasing slowly during the filtering process, and no peak values being reached, due to the compressibility of the air, as a result of which the blood cells are not destroyed at the filter membrane 373 and no undesired hemolysis occurs.

The blood plasma sample P obtained by filtration can either be collected in a collection vessel or transferred directly from the filter 370 into an analysis device, in particular the cartridge 100. In the context of the present invention, the transfer into an analysis device as shown in FIG. 2 is preferred.

FIG. 2 shows the proposed filter 370 or kit 300 in a schematic sectional view before the blood BL to be filtered is conducted to or transferred into the filter 370. In this view, the transfer instrument 320 for preferably providing or transferring the blood sample BL is shown already connected to the filter 370 or to the inlet 376 thereof.

Also shown schematically in FIG. 2 in section is the cartridge 100 provided herein preferably for testing the filtrate, i.e., in particular the blood plasma, as the sample P to be tested, which cartridge 100 is in particular already connected to the filter 370.

Particularly preferably, the filter 370 is directly connected with its outlet 377 to the cartridge 100 or to a receiving cavity 104 or the connection 104A thereof, for example by plugging in or placing on, as shown schematically in FIG. 2.

Particularly preferably, the filtrate or blood plasma is thus dispensed directly from the filter 370 to the cartridge 100 for testing or analysis.

After receiving the sample P in the cartridge 100 and removing the filter 370, the cartridge 100 or receiving cavity 104 or the connection 104A thereof is preferably closed by means of a closure element 130.

By actuating, in particular lowering, the means or piston 322, the blood BL is transferred into the filter 370 and the blood plasma P obtained by filtration is transferred directly into the receiving cavity 104 of the cartridge 100.

The filtration of the blood BL preferably takes place by means of gravity and/or by applying a certain, not excessive pressure.

In the example shown, the filtrate or blood plasma, as the sample P, preferably runs into the cartridge 100 or receiving cavity 104 directly and/or by means of gravity, a corresponding vent (not shown) in particular being formed or provided, preferably between the connection 104A and the outlet 377.

The proposed filter membrane 373 is surface-modified and as a result exhibits substantially improved filtering qualities, the filtrate or blood plasma in particular containing a substantially higher content of metabolic products, in particular peptides, and/or hormones in comparison with a non-surface-treated filter membrane.

The subject matter of the present invention, in particular the surface modification of the filter membrane 373 according to the invention, is illustrated below with reference to an exemplary embodiment.

1. Surface Modification of the Membrane

A sheet having the dimensions 102 mm×140 mm of an asymmetrical, polysulfone-based filter membrane is treated at 20° C. for an hour with a dispersion of 2 wt. % poly(2-hydroxyethyl) methacrylate in ethanol. The surface-modified filter membrane is obtained which is washed with ethanol once for 10 seconds and subsequently dried at 30° C. in a desiccator.

2. Production of the Filter

Circular filter membranes each having a diameter of 42.1 mm are punched out from the surface-modified membrane sheet obtained from method step 1. The filter membranes are adhered into the housing lower part of a filter so as to be flush and the housing lower part is heat sealed to a housing upper part. The filter comprises, on the upper face thereof, an opening that has an adapter for receiving a syringe and, on the lower face thereof, an opening that has an adapter for connection to a collection vessel. The filter has a calculated internal volume of 1350 μl.

3. Checking the Filter

The improved effectiveness of the filter according to the invention is tested in the following on the basis of the peptide hormones ACTH, insulin and leptin. Using non-surface-modified filter membranes, only a maximum of 20% of the content of the above-mentioned peptide hormones are found in the filtered blood plasma in comparison with blood plasma obtained by centrifuging.

50 samples are tested in total. For this purpose, 2 ml of horse blood made incoagulable by means of sodium citrate is withdrawn in each case in a 10 ml Urine Monovette having a lift limitation set at 2.5 ml, such that the Urine Monovettes contain 2 ml of blood and 5.5 ml of air. The Urine Monovettes are subsequently placed onto the adapter at the upper opening of the filter and a collection vessel is attached to the lower outlet opening of the filter. By actuating the piston of the Urine Monovette, pressure is built up such that the blood is pressed into the filter and filtered.

From each individual blood sample, 300 to 350 µl of blood plasma can be obtained which is of clear-yellow color and does not differ visually from plasma obtained from centrifugation. The blood plasma samples are quantitatively evaluated for the three peptide hormones (ACTH, insulin, leptin) by specific and standardized ELISA. In this case, 60 to 70% of the content of peptide hormones that can be detected in the blood plasma from centrifugation are found in every sample.

It is therefore evident that blood plasma can be obtained in a reproducible manner by means of the filter according to the invention, which makes it possible to both qualitatively and quantitatively analyze the components of the blood plasma. The blood plasma obtained by means of the filter according to the invention is therefore suitable for detecting or identifying diseases and metabolic changes.

Figure 3:
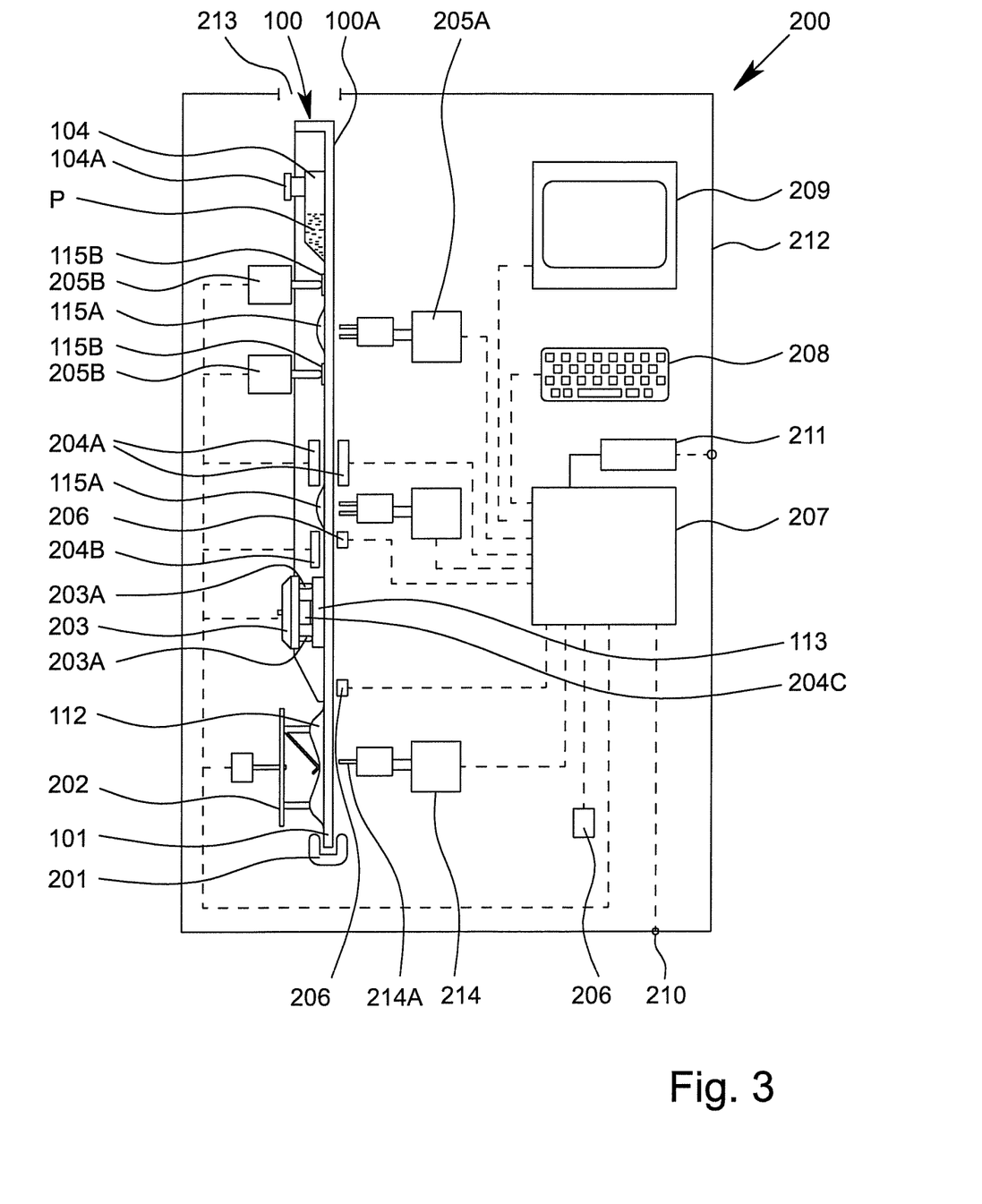
FIG. 3 is a schematic view of a point-of-care system.

FIG. 3 is a highly schematic view of the cartridge 100 in an analysis device 200 for preferred, in particular molecular-biological, testing of the sample P or of the blood plasma.

Figure 4:
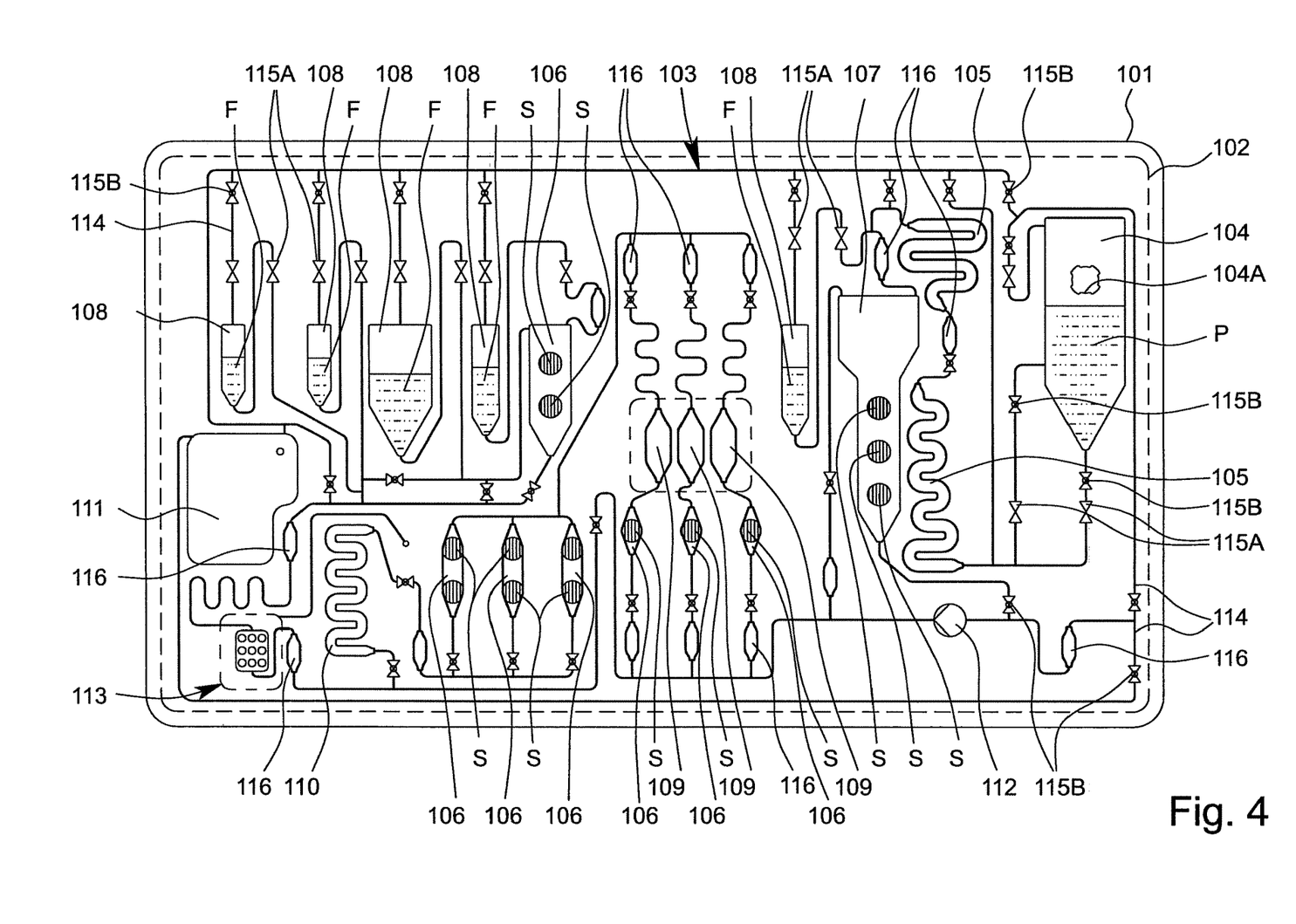
FIG. 4 is a schematic view of an apparatus or cartridge in an analysis device for in particular molecular-biological testing of a blood sample.

FIG. 4 is a schematic plan view of the cartridge 100 for testing the sample P. The cartridge 100 in particular forms a handheld unit which is preferably used only once as a disposable article, as is the case with the filter 370.

The term "cartridge" is preferably understood to mean a structural apparatus or unit designed to receive, to store, to physically, chemically and/or biologically treat and/or prepare and/or to measure a sample, in particular a blood plasma sample P, preferably in order to make it possible to detect, identify or determine at least one analyte, in particular a protein and/or a nucleic-acid sequence, of the sample.

A cartridge within the meaning of the present invention preferably comprises a fluid system having a plurality of channels, cavities and/or valves for controlling the flow through the channels and/or cavities.

In particular, within the meaning of the present invention, a cartridge is designed to be at least substantially planar and/or card-like, in particular is designed as a (micro) fluidic card and/or is designed as a main body or container that can preferably be closed and/or said cartridge can be inserted and/or plugged into a proposed analysis device when it contains the sample.

The term "analysis device" is preferably understood to mean a structural apparatus designed to chemically, biologically and/or physically test and/or analyse a sample or analysis sample or a component thereof, in particular in order for it to be possible to directly and/or indirectly detect or identify a disease and/or pathogen. An analysis device within the meaning of the present invention is in particular a portable or mobile device designed in particular to immediately or directly test and/or analyze the sample, in particular on site and/or in the vicinity of the sampling site and/or away from a central laboratory.

The term "sample" is preferably understood to mean the sample material to be tested, which is in particular taken from a human or animal. In particular, within the meaning of the present invention, a sample is blood plasma, preferably from a human or animal, or a component thereof.

A sample within the meaning of the present invention preferably contains one or more sample components or analytes to be tested, it preferably being possible for the analytes to be identified and/or detected, in particular qualitatively and/or quantitatively determined. Particularly preferably, within the meaning of the present invention, a sample has target nucleic-acid sequences as the analytes, in particular target DNA sequences and/or target RNA sequences, and/or target proteins as the analytes, in particular target antigens and/or target antibodies. Particularly preferably, at least one disease and/or pathogen can be detected or identified in the sample by qualitatively and/or quantitatively determining the analytes.

Preferably, the analysis device 200 controls the testing of the sample P in particular in or on the cartridge 100 and/or the analysis device 200 is used to evaluate the testing and/or to collect, to process and/or to store measured values from the test.

By means of the analysis device 200 and/or by means of the cartridge 100 and/or using the method for testing the sample P, an analyte of the sample P, or particularly preferably a plurality of analytes of the sample P, can preferably be determined, identified or detected. Said analytes are in particular detected, identified and/or measured not only qualitatively, but particularly preferably also quantitatively.

Therefore, the sample P can in particular be tested for qualitatively or quantitatively determining at least one analyte, for example, in order for it to be possible to detect or identify a disease and/or pathogen or to determine other values, which are important for diagnostics, for example.

The cartridge 100 is preferably at least substantially planar, flat, plate-shaped and/or card-like.

The cartridge 100 preferably comprises an in particular at least substantially planar, flat, plate-shaped and/or card-like main body or support 101, the main body or support 101 in particular being made of and/or injection-molded from plastics material, particularly preferably polypropylene.

The cartridge 100 preferably comprises at least one film or cover 102 for covering the main body 101 and/or cavities and/or channels formed therein at least in part, in particular on the front 100A, and/or for forming valves or the like, as shown by dashed lines in FIG. 4.

The cartridge 100 and/or the main body 101 thereof, in particular together with the cover 102, preferably forms and/or comprises a fluidic system 103, referred to in the following as the fluid system 103.

The cartridge 100, the main body 101 and/or the fluid system 103 are preferably at least substantially vertically oriented in the operating position and/or during the test, in particular in the analysis device 200, as shown schematically in FIG. 3. In particular, the main plane or surface extension of the cartridge 100 thus extends at least substantially vertically in the operating position.

The cartridge 100 and/or the fluid system 103 preferably comprises a plurality of cavities, in particular at least one receiving cavity 104, at least one metering cavity 105, at least one intermediate cavity 106, at least one mixing cavity 107, at least one storage cavity 108, at least one reaction cavity 109, at least one intermediate temperature-control cavity 110 and/or at least one collection cavity 111, the cavities preferably being fluidically interconnected by a plurality of channels.

Within the meaning of the present invention, channels are preferably elongate forms for conducting a fluid in a main flow direction, the forms preferably being closed transversely, in particular perpendicularly, to the main flow direction and/or longitudinal extension, preferably on all sides.

In particular, the main body 101 comprises elongate notches, recesses, depressions or the like, which are closed at the sides by the cover 102 and form channels within the meaning of the present invention.

Within the meaning of the present invention, cavities or chambers are preferably formed by recesses, depressions or the like in the cartridge 100 or main body 101, which are closed or covered by the cover 102, in particular at the side. The volume or space enclosed by each cavity is preferably fluidically linked, in particular to the fluid system 103, by means of channels.

In particular, within the meaning of the present invention, a cavity comprises at least two openings for the inflow and/or outflow of fluids.

Within the meaning of the present invention, cavities preferably have a larger diameter and/or flow cross section than channels, preferably by at least a factor of 2, 3 or 4. In principle, however, cavities may in some cases also be elongate, in a similar manner to channels.

The cartridge 100 and/or the fluid system 103 also preferably comprises at least one pump apparatus 112 and/or at least one sensor arrangement or sensor apparatus 113.

The reaction cavity/cavities 109 is/are preferably designed to allow a substance located in the reaction cavity 109 to react when an assay is being carried out, for example by being linked or coupled to apparatuses or modules of the analysis device 200.

The reaction cavity/cavities 109 is/are used in particular to carry out an amplification reaction, in particular PCR, or several, preferably different, amplification reactions, in particular PCRs. It is preferable to carry out several, preferably different, PCRs, i.e., PCRs having different primer combinations or primer pairs, in parallel and/or independently and/or in different reaction cavities 109.

The amplification products, target nucleic-acid sequences and/or other portions of the sample P produced in the one or more reaction cavities 109 can be conducted or fed to the connected sensor arrangement or sensor apparatus 113, in particular by means of the pump apparatus 112.

The sensor arrangement or sensor apparatus 113 is used in particular for detecting or identifying, particularly preferably qualitatively and/or quantitatively determining, the analyte or analytes of the sample P, in this case particularly preferably the target nucleic-acid sequences and/or target proteins as the analytes. Alternatively, or additionally, however, other values may also be collected or determined.

The cartridge 100, the main body 101 and/or the fluid system 103 preferably comprise a plurality of channels 114 and/or valves 115, as shown in FIG. 4.

By means of the channels 114 and/or valves 115, the cavities 104 to 111, the pump apparatus 112 and/or the sensor arrangement or sensor apparatus 113 can be temporarily and/or permanently fluidically interconnected and/or fluidically separated from one another, as required and/or optionally or selectively, in particular such that they are controlled by the analysis device 200.

The cavities 104 to 111 are preferably each fluidically linked or interconnected by a plurality of channels 114. Particularly preferably, each cavity is linked or connected by at least two associated channels 114, in order to make it possible for fluid to fill, flow through and/or drain from the respective cavities as required.

The receiving cavity 104 preferably comprises a connection 104A for introducing the sample P. In the context of the present invention the sample P is usually a blood sample and blood plasma and blood serum is separated by the filter according to the invention. For this purpose, the filter 370 according to the invention is connected with the lower opening or outlet 377, in particular the plasma outlet opening for a suitable connecting piece, to the connection 104A of the receiving cavity 104 of the cartridge 100. In the context of the present invention, the sample P is blood plasma.

The cartridge 100 is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 µl, in particular less than 600 µl or 300 µl, more particularly preferably less than 200 µl or 100 µl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as shown in the schematic view according to FIG. 4.

Furthermore, other liquids F, in particular in the form of a wash buffer, solvent for dry reagents S and/or a substrate, for example in order to form detection molecules and/or a redox system, are also preferably required for the test, the detection process and/or for other purposes, and are in particular provided in the cartridge 100, i.e. are likewise introduced before use, in particular before delivery.

The cartridge 100 preferably contains all the reagents and liquids required for pretreating the sample P and/or for carrying out the test or assay, in particular for carrying out one or more amplification reactions or PCRs, and therefore, particularly preferably, it is only necessary to receive the optionally pretreated sample P.

Once the sample P has been introduced into the receiving cavity 104 and the connection 104A has been closed, the cartridge 100 can be inserted into and/or received in the proposed analysis device 200 in order to test the sample P, as shown in FIG. 3.

The analysis device 200 preferably comprises a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed or sealed fluidic or hydraulic system 103 for the sample P and the reagents and other liquids. In this way, the analysis device 200 does not come into direct contact with the sample P and can in particular be reused for another test without being disinfected and/or cleaned first.

It is however provided that the analysis device 200 is connected or coupled mechanically, electrically, thermally and/or pneumatically to the cartridge 100.

In particular, the analysis device 200 is designed to have a mechanical effect, in particular for actuating the pump apparatus 112 and/or the valves 115, and/or to have a thermal effect, in particular for temperature-controlling the reaction cavity/cavities 109 and/or the intermediate temperature-control cavity 110.

In addition, the analysis device 200 can preferably be pneumatically connected to the cartridge 100, in particular in order to actuate individual apparatuses, and/or can be electrically connected to the cartridge 100, in particular in order to collect and/or transmit measured values, for example from the sensor apparatus 113 and/or from sensor portions 116.

The analysis device 200 preferably comprises a pump drive 202, the pump drive 202 in particular being designed for mechanically actuating the pump apparatus 112.

The analysis device 200 preferably comprises a connection apparatus 203 for in particular electrically and/or thermally connecting the cartridge 100 and/or the sensor arrangement or sensor apparatus 113.

As shown in FIG. 3, the connection apparatus 203 preferably comprises a plurality of electrical contact elements 203A, the cartridge 100, in particular the sensor arrangement or sensor apparatus 113, preferably being electrically connected or connectable to the analysis device 200 by the contact elements 203A.

The analysis device 200 preferably comprises one or more temperature-control apparatuses 204 for temperature-controlling the cartridge 100 and/or having a thermal effect on the cartridge 100, in particular for heating and/or cooling, the temperature-control apparatus(es) 204 (each) preferably comprising or being formed by a heating resistor or a Peltier element.

Preferably, individual temperature-control apparatus 204, some of these apparatus or all of these apparatus can be positioned against the cartridge 100, the main body 101, the cover 102, the sensor arrangement, sensor apparatus 113 and/or individual cavities and/or can be thermally coupled thereto and/or can be integrated therein and/or can be operated or controlled in particular electrically by the analysis device 200. In the example shown, in particular the temperature-control apparatus 204A, 204B and/or 204C are provided.

The analysis device 200 preferably comprises one or more actuators 205 for actuating the valves 115. Particularly preferably, different (types or groups of) actuators 205A and 205B are provided which are assigned to the different (types or groups of) valves 115A and 115B for actuating each of said valves, respectively.

The analysis device 200 preferably comprises one or more sensors 206. In particular, sensors 206 are assigned to the sensor portions 116 and/or are designed or provided for detecting liquid fronts and/or flows of fluid in the fluid system 103, the ambient temperature, internal temperature, atmospheric humidity, position, and/or alignment, for example by means of a GPS sensor, and/or the orientation and/or inclination of the analysis device 200 and/or the cartridge 100.

The analysis device 200 preferably comprises a control apparatus 207, in particular comprising an internal clock or time base for controlling the sequence of a test or assay and/or for collecting, evaluating and/or outputting or providing measured values in particular from the sensor apparatus 113, and/or from test results and/or other data or values.

The control apparatus 207 preferably controls or feedback controls the pump drive 202, the temperature-control apparatuses 204 and/or actuators 205, in particular taking into account or depending on the desired test and/or measured values from the sensor arrangement or sensor apparatus 113 and/or sensors 206.

Optionally, the analysis device 200 comprises an input apparatus 208, such as a keyboard, a touch screen or the like, and/or a display apparatus 209, such as a screen.

The analysis device 200 preferably comprises at least one interface 210, for example for controlling, for communicating and/or for outputting measured data or test results and/or for linking to other devices, such as a printer, an external power supply or the like. This may in particular be a wired or wireless interface 210.

The analysis device 200 preferably comprises a power supply 211 for providing electrical power, preferably a battery or an accumulator, which is in particular integrated and/or externally connected or connectable.

The analysis device 200 preferably comprises a housing 212, all the components and/or some or all of the apparatuses preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis device 200 is preferably portable or mobile. Particularly preferably, the analysis device 200 weighs less than 25 kg or 20 kg, particularly preferably less than 15 kg or 10 kg, in particular less than 9 kg or 6 kg.

Individual aspects and features of the present invention and individual method steps and/or variants of the method may be implemented independently from one another, but also in any desired combination and/or order.

What is claimed is:

1. Filter for separating blood plasma and blood serum from a blood sample, comprising a filter membrane surface-coated with a modifying agent for separating blood plasma and blood serum, wherein the modifying reagent is a hydrogel former and is a poly(hydroxyethyl) methacrylate or a copolymer of 2-hydroxyethyl methacrylate, wherein the surface is coated by treating the surface with a solution or dispersion of the modifying reagent that contains the modifying reagent in quantities of 1 to 2 wt. %, based on the solution or dispersion, for a period of 30 minutes to 5 hours, wherein the filter membrane is a porous asymmetrical membrane, and wherein the material of the filter membrane comprises at least one of the following polymers: polyamide, polyethylene terephthalate, polysulfone, polyether sulfone, polyvinyl pyrrolidone, polyurethane, polyacrylonitrile, poly(vinylidene fluoride), polytetrafluoroethylene, polyacrylonitrile-methacrylate copolymer, cellulose, modified cellulose, cellulose ether and mixtures and copolymers thereof, provided that the filter membrane comprises at least one hydrophilic polymer, and wherein the filter comprises a filter upper part and a filter lower part, the filter lower part having a convex curvature.

2. Kit for testing blood plasma, comprising a filter with a filter membrane surface-coated with a modifying agent for separating blood plasma and blood serum from a blood sample, wherein the modifying reagent is a hydrogel former and is a poly(hydroxyethyl) methacrylate or a copolymer of 2-hydroxyethyl methacrylate, wherein the surface is coated by treating the surface with a solution or dispersion of the modifying reagent, that contains the modifying reagent in quantities of 1 to 3 wt. %, based on the solution or dispersion, for a period of 30 minutes to 5 hours, wherein the filter membrane is a porous asymmetrical membrane, wherein the material of the filter membrane comprises a polymer from among the following polymers: polyamide, polyethylene terephthalate, polysulfone, polyether sulfone, polyvinyl pyrrolidone, polyurethane, polyacrylonitrile, poly(vinylidene fluoride), polytetrafluoroethylene, polyacrylonitrile-methacrylate copolymer, cellulose, modified cellulose, cellulose ether and mixtures and copolymers thereof, and wherein the filter comprises a filter upper part and a filter lower part, the filter lower part having a convex curvature, the kit further comprising a cartridge, wherein the cartridge comprises a main body having a plurality of channels and cavities, including a receiving cavity, wherein the cartridge comprises a cover for the channels and cavities, and wherein the cartridge has a connection for connecting an outlet of the filter to the receiving cavity of the cartridge.

\* \* \* \* \*